United States Patent [19]

Crowley

[11] Patent Number: 4,895,974
[45] Date of Patent: Jan. 23, 1990

[54] FUNGICIDES

[75] Inventor: Patrick J. Crowley, Crowthorne, England

[73] Assignee: Imperial Chemical Industries PLC, London, England

[21] Appl. No.: 194,692

[22] Filed: May 16, 1988

[30] Foreign Application Priority Data

May 15, 1987 [GB] United Kingdom ............... 8711538

[51] Int. Cl.$^4$ ............................................. C07C 69/76
[52] U.S. Cl. ..................................... 560/060; 560/23; 558/414
[58] Field of Search .................... 560/60, 23; 558/414; 574/532, 538

[56] References Cited

FOREIGN PATENT DOCUMENTS 0178826 4/1986 European Pat. Off. .

Primary Examiner—Paul J. Killos
Attorney, Agent, or Firm—Cushman, Darby & Cushman

[57] ABSTRACT

Compounds of formula:

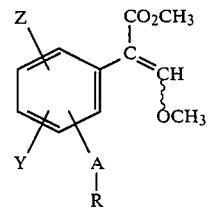

and stereoisomers thereof, in which A is oxygen or sulphur; Z and Y are independently hydrogen, halogen, optionally substituted alkyl, nitro or cyano; and R, which contains at least one halogen atom, is the group

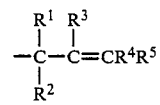

in which $R^1$ and $R^2$ are independently hydrogen or alkyl; and $R^3$, $R^4$ and $R^5$ are independently hydrogen, halogen, alkyl, haloalkyl or alkoxy.

8 Claims, No Drawings

FUNGICIDES

This invention relates to derivatives of propenoic acid useful as fungicides, to processes for preparing them, to fungicidal compositions containing them, and to methods of combating fungi, especially fungal infections in plants, using them.

The compound (E)-methyl-2-(2-allyloxy)phenyl-3-methoxypropenoate is disclosed as a fungicide in EP-A-0178826.

The present invention provides improved fungicidal compounds having the formula (I):

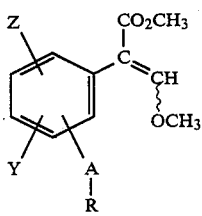

and stereoisomers thereof, in which A is oxygen or sulphur; Z and Y are independently hydrogen, halogen, optionally substituted alkyl, nitro or cyano; and R, which contains at least one halogen atom, is the group

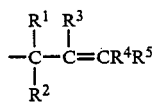

in which $R^1$ and $R^2$ are independently hydrogen or alkyl; and $R^3$, $R^4$ and $R^5$ are independently hydrogen, halogen, alkyl, haloalkyl or alkoxy.

Owing to the presence of the olefinic double bonds in the propenoate group and in the group R, the compounds of the invention may be obtained in the form of mixtures of geometric isomers. However, these mixtures can be separated into individual isomers e.g. by conventional chromatographic techniques, and this invention embraces such isomers, and mixtures thereof in all proportions. In particular, it includes mixtures which consist substantially of the (Z)-isomers with respect to the propenoate group and those which consist substantially of the (E)-isomers with respect to the propenoate group.

The individual isomers which result from unsymmetrically substituted double bonds group are identified by the commonly used terms "(E)" and "(Z)". These terms are defined according to the Cahn-Ingold-Prelog system which is fully described in the literature (see, for example, J March, "Advanced Organic Chemistry", 3rd edition, Wiley-Interscience, page 109 et seq).

Usually one isomer with respect to the propenoate group is more active fungicidally than the other, the more active isomer usually being the one wherein the groups —$CO_2CH_3$ and —$OCH_3$ are on opposite sides of the olefinic bond (the (E)-isomer). These (E)-isomers form a preferred embodiment of the invention.

The terms "halogen" and "halo" wherever used include fluorine, chlorine, bromine and iodine. When Z and/or Y are halogen preferably they are fluorine or chlorine. When $R^3$, $R^4$ and/or $R^5$ are halogen preferably they are chlorine or bromine. Haloalkyl is preferably fluoroalkyl or chloroalkyl, especially trifluoromethyl or trichloromethyl.

Alkyl groups or the alkyl moiety of alkoxy groups are preferably $C_{1-4}$ alkyl and can be in the form of straight or branched chains. Examples are methyl, ethyl, n- and isopropyl, and n-, sec-, iso- and t-butyl.

Where the alkyl group is substituted, substituents include halogen (preferably fluorine or chlorine), hydroxy and $C_{1-4}$ alkoxy. A preferred optionally substituted alkyl group is trifluoromethyl.

In a preferred aspect, the invention provides the (E)isomers (with respect to the propenoate group) of compounds of the formula (Ia):

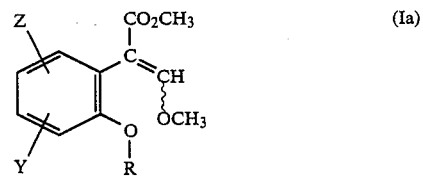 (Ia)

in which Z and Y are independently hydrogen or halogen (preferably fluorine or chlorine), $C_{1-4}$ alkyl (preferably methyl), nitro, cyano or trifluoromethyl; and R, which contains at least one halogen atom is the group

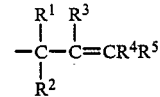

in which $R^1$ and $R^2$ are independently hydrogen or $C_{1-4}$ alkyl (preferably methyl) and $R^3$, $R^4$ and $R^5$ are independently hydrogen, chlorine, bromine or iodine, $C_{1-4}$ alkyl (preferably methyl), halo($C_{1-4}$)alkyl (preferably fluoro- or chloro-alkyl) or $C_{1-4}$ alkoxy (preferably methoxy).

In a particularly preferred aspect, the invention provides the (E)-isomers (with respect to the propenoate group) of compounds of the formula (Ib):

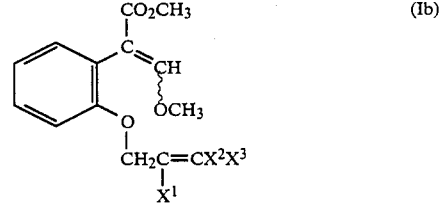 (Ib)

in which $X^1$, $X^2$ and $X^3$ are independently hydrogen, chlorine, bromine or iodine provided at least one is halogen.

Especially preferred are the compounds (Ib) in which $X^1$, $X^2$ and $X^3$ are independently hydrogen, chlorine or bromine provided at least one is chlorine or bromine.

The compounds of the invention are illustrated in Table I which follows.

TABLE I

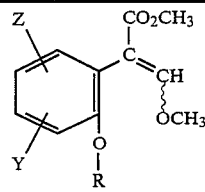

| COMPOUND NO. | R | Y | Z | MELTING POINT | OLEFINIC | ISOMER |
|---|---|---|---|---|---|---|
| 1 | 3,3-dichloroprop-2-enyl | H | H | Oil | 7.48 | E |
| 2 | 3,3-dibromoprop-2-enyl | H | H | Oil | 7.50 | E |
| 3 | (E)-2,3-dichloroprop-2-enyl | H | H | | | E |
| 4 | (Z)-2,3-dichloroprop-2-enyl | H | H | | | E |
| 5 | (E)-2,3-dibromoprop-2-enyl | H | H | Oil* | 7.52* | E |
| 6 | (Z)-2,3-dibromoprop-2-enyl | H | H | Oil* | 7.52* | E |
| 7 | (E)-2,3-diiodoprop-2-enyl | H | H | | | E |
| 8 | (Z)-2,3-diiodoprop-2-enyl | H | H | | | E |
| 9 | (E)-3-chloroprop-2-enyl | H | H | | | E |
| 10 | (E)-3-bromoprop-2-enyl | H | H | | | E |
| 11 | 2-chloroprop-2-enyl | H | H | Oil | 7.54 | E |
| 12 | 2-bromoprop-2-enyl | H | H | | | E |
| 13 | (E)-3-bromo-3-chloroprop-2-enyl | H | H | | | E |
| 14 | (Z)-3-bromo-3-chloroprop-2-enyl | H | H | | | E |
| 15 | 2,3,3-trichloroprop-2-enyl | H | H | | | E |
| 16 | 2,3,3-tribromoprop-2-enyl | H | H | | | E |
| 17 | 2,3,3-triiodoprop-2-enyl | H | H | | | E |
| 18 | (E)-2-chloro-3-iodoprop-2-enyl | H | H | | | E |
| 19 | (Z)-2-chloro-3-iodoprop-2-enyl | H | H | | | E |
| 20 | (E)-4,4,4-trifluorobut-2-enyl | H | H | | | E |
| 21 | (E)-3-chloro-4,4,4-trifluorobut-2-enyl | H | H | | | E |
| 22 | (Z)-3-chloro-4,4,4-trifluorobut-2-enyl | H | H | | | E |
| 23 | 4,4-dichlorobut-3-ene-2-yl | H | H | | | E |
| 24 | 4,4-dibromobut-3-ene-2-yl | H | H | | | E |

*5 and 6 in admixture (1:1)

The compounds of the invention of formula (I) may be prepared by the steps shown in Schemes I and II. Throughout these Schemes the terms R, A, Y and Z are as defined above, V is hydrogen or a metal (such as sodium or potassium), W is an alkyl group and L is a leaving group such as halide (chloride, bromide or iodide), a $CH_3SO_4$-anion, or a sulphonyloxy-anion. Each of the transformations described in Schemes I and II is performed at a suitable temperature and usually, though not always, in a solvent.

The compounds of the invention of formula (I) can be prepared from the phenylacetates of formula (V) by the steps shown in Scheme I.

Thus compounds of formula (I) can be prepared by treatment of phenylacetates of formula (V) with a base (such as sodium hydride or sodium methoxide) and methyl formate. If a species of formula $CH_3L$, wherein L is as defined above, is then added to the reaction mixture, compounds of formula (I) may be obtained. If a protic acid is added to the reaction mixture, compounds of formula (IV) wherein V is hydrogen are obtained. Alternatively, the species of formula (IV) wherein V is a metal (such as sodium) may themselves be isolated from the reaction mixture.

Compounds of formula (IV) wherein V is a metal can be converted into compounds of formula (I) by treatment with a species of formula $CH_3L$, wherein L is as defined above. Compounds of formula (IV) wherein V is hydrogen can be converted into compounds of formula (I) by successive treatments with a base (such as potassium carbonate) and a species of formula $CH_3L$.

Alternatively, compounds of formula (I) can be prepared from acetals of formula (II) by elimination of methanol under either acidic or basic conditions. Examples of reagents or reagent mixtures which can be used for this transformation are lithium di-isopropylamide; potassium hydrogen sulphate (see, for example, T. Yamada, H. Hagiwara and H. Uda, *J. Chem. Soc., Chemical Communications*, 1980, 838, and references therein); and triethylamine, often in the presence of a Lewis acid such as titanium tetrachloride (see, for example, K. Nsunda and L. Heresi, *J. Chem. Soc., Chemical Communications*, 1985, 1000).

Acetals of formula (II) can be prepared by treatment of methyl silyl ketene acetals of formula (III), wherein W is an alkyl group, with trimethyl orthoformate in the presence of a Lewis acid such as titanium tetrachloride (see, for example, K. Saigo, M. Osaki and T. Mukaiyama, *Chemistry Letters*, 1976, 769).

Methyl silyl ketene acetals of formula (III) can be prepared from phenylacetates of formula (V) by treatment with a base and a trialkylsilyl halide of formula $W_3SiCl$ or $W_3SiBr$, such as trimethylsilyl chloride, or a base (such as triethylamine) and a trialkylsilyl triflate of formula $W_3Si\text{-}OSO_2CF_3$ (see, for example, C. Ainsworth, F. Chen and Y. Kuo, *J. Organometallic Chemistry*, 1972, 46, 59).

It is not always necessary to isolate the intermediates (II) and (III); under appropriate conditions, compounds of formula (I) may be prepared from phenylacetates of formula (V) in "one pot" by the successive additions of suitable reagents listed above.

Compounds of formula (V) may be prepared from phenylacetates of formula (VI) by reaction with a species of formula RL, wherein R and L are as defined above, in the presence of a base (such as potassium carbonate) and, if necessary, a transition metal salt catalyst (such as copperbronze) in a convenient solvent (such as N,N-dimethylformamide).

The acetates (VI) may be prepared by esterification of the parent acids by standard methods described in the chemical literature.

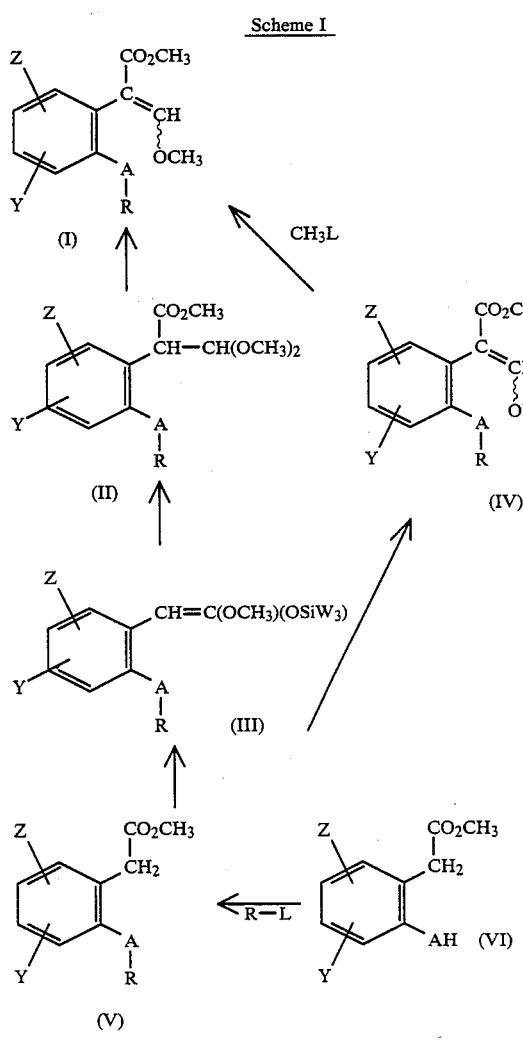

Alternatively, compounds of the invention having the general formula (I) can be prepared from phenylacetates of general formula (XI) by the steps shown in Scheme II. Throughout Scheme II the terms R, A, Y, Z and L are as defined above, and M is a protecting group for a phenol or thiophenol group.

Thus compounds of general formula (I) can be prepared by reaction of compounds of general formula (VIII) with a compound RL in the presence of a base (such as potassium carbonate) and, if necessary, a transition metal or transition metal salt catalyst in a convenient solvent (such as N,N-dimethylformamide).

Scheme II

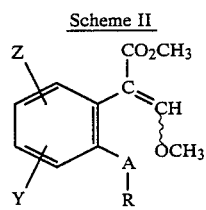

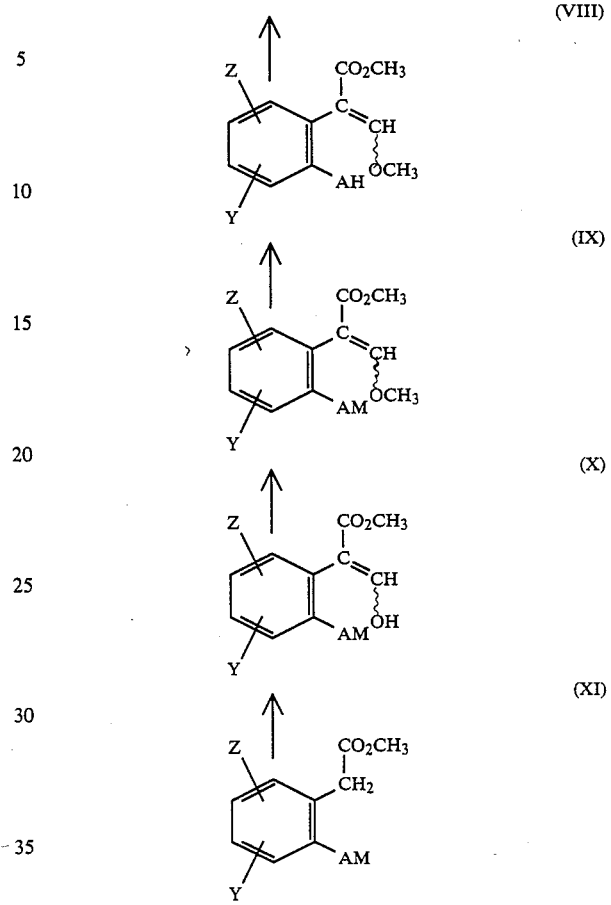

Compounds of general formula (VIII) can be prepared from protected phenol or thiophenyl derivatives of general formula (IX) by standard deprotection procedures as set out in the chemical literature. For example, phenols of general formula (VIII, A is O) can be prepared from benzyl ethers of general formula (IX, A is O, M is benzyl) by hydrogenolysis in the presence of a suitable catalyst (such as palladium supported on carbon).

Compounds of general formula (IX), in which the group M is a standard phenol or thiophenyl protecting group (such as benzyl), can be prepared by O-methylation of compounds of general formula (X) using a base (such as potassium carbonate) and a methylating agent CH₃-L in a suitable solvent (such as N,N-dimethylformamide)

Compounds of general formula (X) can be prepared by treating phenylacetates of general formula (XI) with a base (such as sodium hydride) and a formic ester (such as methyl formate) in a suitable solvent (such as N,N-dimethylformamide).

Compounds of general formula (XI) can be prepared from compounds of general formula (VI) by standard methods described in the chemical literature.

The compounds of the invention are active fungicides, and may be used to control one or more of the following pathogens:

*Pyricularia oryzae* on rice,
*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Ersiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apples and *Uncinula necator* on vines.

*Helminthosporium* spp., *Rhynchosporium* spp., *Septoria* spp., *Pseudocercosporella herpotrichoides* and *Gaeumannomyces graminis* on cereals.

*Cercospora arachidicola* and *Cercosporidium personata* on peanuts and other *Cercospora* species on other hosts for example sugar beet, bananas, soya beans and rice.

*Botrytis cinerea* (grey mould) on tomatoes, strawberries, vegetables, vines and other hosts.

*Alternaria* species on vegetables (e.g. cucumber), oil seed rape, apples, tomatoes and other hosts.

*Venturia inaequalis* (scab) on apples.

*Plasmopara viticola* on vines.

Other downy mildews such as *Bremia lactucae* on lettuce, *Peronospora* spp. on soybeans, tobacco, onions and other hosts and *Pseudoperonospora humuli* on hops and *Pseudoperonospora cubensis* on cucurbits.

*Phytophthora infestans* on potatoes and tomatoes and other *Phytophthora* spp. on vegetables, strawberries, avocado, pepper, ornamentals, tobacco, cocoa and other hosts.

*Thanatephorus cucumeris* on rice and other *Rhizoctonia* species on various host such as wheat and barley, vegetables, cotton and turf.

The compounds may have activity against various post-harvest diseases of fruit (e.g. *Penicillium digitatum* and *italicum* and *Trichoderma viride* on oranges and *Gloeosporium musarum* on bananas).

Further some of the compounds may be active as seed dressings against *Fusarium* spp., *Septoria* spp., *Tilletia* spp., (bunt, a seed borne disease of wheat), *Ustilago* spp., *Helminthosporium* spp. on cereals, *Rhizoctonia solani* on cotton and *Pyricularia oryzae* on rice.

The compounds may be volatile enough to be active in the vapour phase against fungi on the plant.

The compounds may also be useful as industrial (as opposed to agricultural) fungicides, e.g. in the prevention of fungal attack on wood, hides, leather and especially paint films.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

The invention also provides a method of combating fungi, which comprises applying to a plant, to seed of a plant, or to the locus of the plant or seed, a compound as hereinbefore defined, or a composition containing the same.

The compounds, can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate the dispersion in liquids The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear diseases of cereals (e.g. wheat) such as *Septoria*, *Gibberella* and *Helminthosporium* spp., seed and soil borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(1-cyano-1-ethoxymethyl)benzamide, benalaxyl, fosetyl-aluminium, fenarimol, iprodione, prothiocarb, procymidone, vinclozolin, penconazole, myclobutanil, propamocarb, R0151297, diconazole, pyrazophos, ethirimol, ditalimfos, tridemorph, triforine, nuarimol, triazbutyl, guazatine, triacetate salt of 1,1'-iminodi(octamethylene)diquanidine, buthiobate, propiconazole, prochloraz, flutriafol, hexaconazole, (2 RS, 3 RS)-2-(4-chlorophenyl)-3-cyclopropyl-1-(1H-1,2,4-triazol-1-yl)butan-2-ol, (RS)-1-(4-chloro-phenyl)-4,4-dimethyl-3-(1H-1,2,4-triazol-1-ylmethyl)pentan-3-ol, flusilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, pyroguilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, streptomycin, hydroxyisoxazole, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, binapacryl, dichlone, chloroneb, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfid, triapenthenol and tecnazane.

The following Examples illustrate the invention. In the Examples NMR data are selective; no attempt is made to list every absorption. $^1$H NMR spectra were recorded using CDCl$_3$ solution. The following abbreviations are used throughout:

NMR = nuclear magnetic resonance
s = singlet
d = doublet
t = triplet
m = multiplet

EXAMPLE 1

This Example illustrates the preparation of (E)-methyl 2-[2'-(3''-dichloroprop-2''-enyloxy)phenyl]-3-methoxypropenoate (Compound No. 1 of Table I).

To a stirred solution of (E)-methyl 2-[2'-hydroxyphenyl]-3-methoxypropenoate (0.208 g) in acetonitrile, potassium carbonate (0.070 g) was added followed by 3,3-dichloroprop-2-enyl bromide (0.190 g) in acetonitrile (1 ml) and a few crystals of potassium iodide. The mixture was stirred at room temperature for two hours and was then left to stand overnight. A few further crystals of potassium iodide were added. Stirring was continued for a further eight hours and then the mixture left to stand again overnight. A few more crystals of potassium iodide were added, the mixture again stirred for several hours and then poured into water, and extracted with ethyl acetate. The organic fractions were combined, washed with dilute sodium hydroxide and then water, and were dried over magnesium sulphate. After evaporation a brownish oil was obtained (0.320 g) which was purified by preparative thin layer chromatography eluting with 1:1 ether:hexane. The desired product (E)-methyl 2-[2'-(3'',3''-dichloroprop-2''-enyloxy)phenyl]-3methoxypropenoate was obtained as a colourless oil (0.140 g); $^1$H NMR delta 3.70 (s,3H); 3.76 (s,3H); 4.62 (d,2H); 6.08 (t,1H); 6.80–7.60 (m,4H); 7.48 (s,1H).

EXAMPLE 2

This Example illustrates the preparation of Compound Nos. 5 and 6 of Table I, as a mixture of dibromo-(E)- and (Z)-isomers, about the propenyloxy double bond.

Methyl 2-hydroxyphenyl acetate (0.99 g), potassium carbonate (0.90 g) and 1,2,3-tribromoprop-2-ene (2.19 g of a mixture of (E)- and (Z)-isomers) were refluxed in methanol (60 ml) for 1.5 hours. The mixture was then cooled, filtered, and the filtrate evaporated to give an orange brown oil, which was partioned between ether and dilute hydrochloric acid. The ether layer was washed with water, dried over magnesium sulphate and the ether fraction evaporated to give methyl 2-(2,3-dibromoprop-2-enyloxy)phenyl acetate, as a mixture of (E)- and (Z)-isomers (2.147 g), of sufficient purity to carry through to the next stage without purification. $^1$H NMR (CDCl$_3$) of mixture of (E)- and (Z)-isomers; delta 3.66, 3.68, 3.69, 3.72 (all singlets, totalling 5H); 4.68, 4.71, 4.88 (all singlets, totalling 2H); 6.66–7.30 (m, 5H).

Infrared maximum (film): 2220, 1740 cm$^{-1}$.

Trimethylsilyl triflate (0.92 g) was added dropwise to a solution of triethylamine (0.42 g) in methylene chloride (15 ml) at room temperature under nitrogen. After ten minutes the clear pinkish solution was added dropwise with stirring at 0° C. under nitrogen, to a solution of methyl 2(2,3-dibromoprop-2-enyloxy)phenyl acetate (1.0 g of a mixture of (E)- and (Z)-isomers) in methylene chloride (15 ml), and the whole mixture stirred at room temperature for 2 hours, and then stood overnight, to give a solution of the silyl enol ethers.

Separately, trimethylorthoformate (0.44 g) in methylene chloride (20 ml) was stirred at −70° C. under nitrogen, while titanium tetrachloride (0.78 g) in methylene chloride (10 ml) was added dropwise. After completion of the addition the yellow suspension was stirred at −70° C. for 15 minutes. To this suspension was added the previously prepared solution of the silyl enol ethers, dropwise over 10 minutes, and then the mixture warmed slowly to room temperature. After standing for 4 days, the solution was poured into 5% aqueous potassium carbonate and the methylene chloride layer separated The aqueous fraction was extracted further with ether, and the ether and methylene chloride dried over magnesium sulphate and evaporated to give a brown oil (0.97 g). This was purified by HPLC (eluent ethyl acetate:hexane, 3:7) to give (E)-methyl 2-[2'-(2'',3''-dibromoprop-2''-enyloxy)phenyl]-3-methoxypropenoate as an approximately 1:1 mixture of (E)- and (Z)-dibromo isomers about the propenyl double bond, Compound Nos. 5 and 6 from Table I, (0.122 g) $^1$H NMR (CDCl$_3$) of mixture of Compound Nos. 5 and 6 from Table I; delta 3.70 (s, 3H); 3.83 (s, 3H), 4.67 (s, 2H), 4.81 (s, 2H), 6.67–7.31 (m, 5H), 7.52 (s, 1H).

Infrared maximum (film): 1710, 1640 cm$^{-1}$.

EXAMPLE 3

This Example illustrates the preparation of Compound No. 11 of Table I.

Methyl 2-hydroxyphenyl acetate (1.50 g) and potassium carbonate (1.38 g) were stirred in methanol (20 ml) for 0.5 hour at room temperature, and then neat 2,3-dichloroprop-1-ene (1.22 g) was added. The mixture was stirred at room temperature for 5 hours, refluxed for 0.75 hour, cooled overnight and then refluxed for a further 2 hours. After filtration the filtrate was evaporated to give a red gum which was dissolved in ethyl acetate and washed with aqueous potassium carbonate, and then water, and then dried over magnesium sulphate. Evaporation yielded a brown semisolid, which was purified by chromatography on silica gel (eluent methylene chloride) to give methyl 2-(2-chloroprop-2-enyloxy)phenyl acetate as a clear yellow liquid (0.37 g). $^1$H NMR (CDCl$_3$); delta 3.70 (s, 5H); 4.60 (s, 2H); 5.44 (d, 1H); 5.58 (d, 1H); 6.84 (d, 1H); 6.98 (t, 1H); 7.24 (t of d, 2H).

Infrared maximum (film) : 1740, 1640 cm$^{-1}$.

A mixture of methyl 2-(2-chloroprop-2-enyloxy)phenyl acetate (0.31 g) and methyl formate (0.72 g), in dry DMF (2 ml), was added dropwise over 5 minutes with stirring, to sodium hydride (0.13 g of a 50% dispersion in oil which was washed with 40:60 petroleum ether prior to use) in dry DMF (5 ml) at 0°–10° C. The dark brown mixture was kept at 0°–5° C. for 1 hour, at room temperature for 1 hour, and then poured into water and extracted with ethyl acetate. The aqueous layer was then acidified with concentrated hydrochloric acid to pH 1–2, and extracted with methylene chloride. This extract was dried over magnesium sulphate and evaporated to yield a yellow mobile liquid (3.90 g) which was dissolved in DMF (10 ml), and potassium carbonate (0.36 g) added After stirring at room temperature for 0.5 hour, dimethyl sulphate (0.20 g) was added dropwise over 1–2 minutes, stirred at room temperature for 0.5 hour, and then stood overnight. The reaction mixture was then poured into water and extracted with ethyl acetate The ethyl acetate extract was washed with brine, dried over magnesium sulphate and evaporated to give a red-brown oil (0.25 g). This oil was purified by chromatography on silica gel (eluent 2:1, hexane:ether) to yield (E)-methyl 2-[2'-(2''- chloroprop-2''-enyloxy)-phenyl]-3-methoxy propenoate as a clear yellow gum (0.071 g). $^1$H NMR (CDCl$_3$); delta 3.70 (s, 3H); 3.83 (s, 3H), 4.56 (s, 2H); 5.40 (s, 1H), 5.54 (s, 1H); 6.88 (d, 1H); 7.02 (t, 1H); 7.20–7.32 (m, 2H); 7.54 (s, 1H).

Infrared maximum (film) : 1715, 1645 cm$^{-1}$.

The following are Examples of compositions suitable for agricultural and horticultural purposes which can be formulated from the compounds of the invention. Such compositions form another aspect of the invention. Percentages are by weight.

EXAMPLE 4

An emulsifiable concentrate is made up by mixing and stirring the ingredients until all are dissolved.

| | |
|---|---|
| Compound No. 1 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 5

The active ingredient is dissolved in methylene dichloride and the resultant liquid sprayed on to the granules of attapulgite clay. The solvent is then allowed to evaporate to produce a granular composition.

| | |
|---|---|
| Compound No. 1 of Table I | 5% |
| Attapulgite granules | 95% |

EXAMPLE 6

A composition suitable for use as a seed dressing is prepared by grinding and mixing the three ingredients.

| | |
|---|---|
| Compound No. 1 of Table I | 50% |
| Mineral oil | 2% |
| China clay | 48% |

EXAMPLE 7

A dustable powder is prepared by grinding and mixing the active ingredient with talc.

| | |
|---|---|
| Compound No. 1 of Table I | 5% |
| Talc | 95% |

EXAMPLE 8

A suspension concentrate is prepared by ball milling the ingredients to form an aqueous suspension of the ground mixture with water.

| | |
|---|---|
| Compound No. 1 of Table I | 40% |
| Sodium lignosulphonate | 10% |
| Bentonite clay | 1% |
| Water | 49% |

This formulation can be used as a spray by diluting into water or applied directly to seed.

EXAMPLE 9

A wettable powder formulation is made by mixing together and grinding the ingredients until all are thoroughly mixed.

EXAMPLE 10

Compound Nos. 1 and 2 (Table I) were tested against a variety of foliar fungal diseases of plants. The technique employed was as follows.

The plants were grown in John Innes Potting Compost (No 1 or 2) in 4 cm diameter minipots. The formulated test compound was diluted to the required concentration immediately before use. The formulation (25 ppm active ingredient) was sprayed onto the foliage. The sprays were applied to maximum retention. Tween 20, to give a final concentration of 0.05%, was added when the sprays were applied to cereals.

For most of the tests the compound was applied to the foliage (by spraying) one or two days before the plant was inoculated with the disease An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace–5% of disease on untreated plants
2 = 6–25% of disease on untreated plants
1 = 26–59% of disease on untreated plants
0 = 60–100% of disease on untreated plants By way of comparison only, the compound (E)-methyl 2-(2-allyloxy)phenyl-3-methoxypropenoate (referred to as the "comparative compound") was tested in a similar way.

Test results are shown in Table II.

The results show that the dichloro- and dibromosubstituted propenyloxyphenylmethoxypropenoate compounds of the invention show superior fungicidal activity to the unsubstituted comparative compound.

TABLE II

| COMPOUND NO. (TABLE I) | PUCCINIA RECONDITA | ERYSIPHE GRAMINIS | VENTURIA INAEQUALIS | PLASMOPARA VITICOLA |
|---|---|---|---|---|
| 1 | 4 | 4 | 4 | 4 |
| 2 | 4 | 4 | 4 | 4 |
| Comparative Compound | 0 | 0 | 0 | 0 |

I claim:

1. A compound of the formula (I):

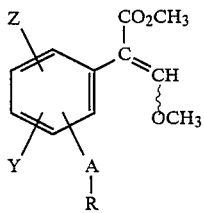

and stereoisomers thereof, in which A is oxygen or sulphur; Z and Y are independently hydrogen, halogen, optionally substituted alkyl, nitro or cyano; and R, is the group

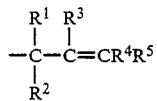

in which $R^1$ and $R^2$ are independently hydrogen or alkyl; and $R^3$, $R^4$ and $R^5$ are independently hydrogen, halogen, alkyl, haloalkyl or alkoxy provided at least one of $R^4$ and $R^5$ is halogen.

2. An (E)-isomer (with respect to the propenoate group) of a compound of the formula (Ia):

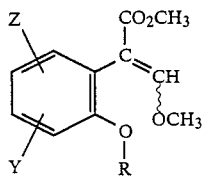

in which Z and Y are independently hydrogen or halogen, $C_{1-4}$ alkyl, nitro, cyano or trifluoromethyl; and R is the group

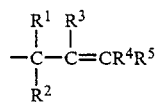

in which $R^1$ and $R^2$ are independently hydrogen or $C_{1-4}$ alkyl and $R^3$, $R^4$ and $R^5$ are independently hydrogen, chlorine, bromine or iodine, $C_{1-4}$ alkyl, halo($C_{1-4}$)-alkyl or $C_{1-4}$ alkoxy provided at least one of $R^4$ and $R^5$ is halogen.

3. An (E)-isomer (with respect to the propenoate group) of a compound of the formula (Ib):

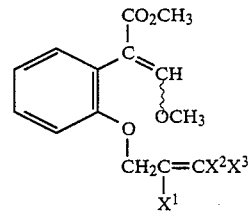

in which $X^1$, $X^2$ and $X^3$ are independently hydrogen, chlorine or bromine or iodine provided at least one of $X^2$ and $X^3$ is halogen.

4. A compound according to claim 3 in which $X^1$, $X^2$ and $X^3$ are independently hydrogen, chlorine or bromine provided at least one of $X^2$ and $X^3$ is chlorine or bromine.

5. A process for preparing compounds according to claim 1 which comprises:
(i) treating a compound of formula (IV):

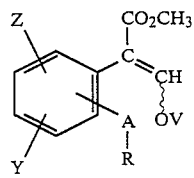

wherein V is a metal atom with a compound $CH_3L$ or wherein V is hydrogen, successively with a base and a compound $CH_3L$; or
(ii) eliminating the elements of methanol from an acetal of formula (II):

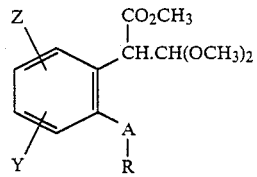

under either acidic or basic conditions; or
(iii) reacting a compound of formula (VIII):

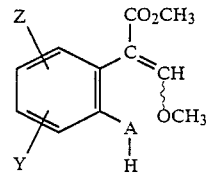

with a compound RL in the presence of a base and optionally a transition metal or transition metal salt catalyst in a convenient solvent; wherein A, R, Y and Z have the meanings given in claim 1 and L is a leaving group.

6. A fungicidal composition comprising a fungicidally effective amount of a compound according to claim 1 and a fungicidally acceptable carrier or diluent therefor.

7. A method of combating fungi which comprises applying to plants or seeds, or to their locus, an effective amount of a compound according to claim 1.

8. A compound according to claim wherein A is oxygen and Z and Y are both hydrogen and R is 3,3-dichloroprop-2-enyl.

* * * * *